(12) United States Patent  
Nakamura et al.

(10) Patent No.: US 10,589,262 B2
(45) Date of Patent: Mar. 17, 2020

(54) METHOD OF PRODUCING PROTON PUMP INHIBITOR COMPOUND HAVING OPTICAL ACTIVITY

(71) Applicants: THE UNIVERSITY OF TOKYO, Tokyo (JP); TOWA PHARMACEUTICAL CO. LTD., Osaka (JP)

(72) Inventors: Eiichi Nakamura, Tokyo (JP); Laurean Ilies, Tokyo (JP); Yoji Oderaotoshi, Osaka (JP); Takuhiro Izumi, Osaka (JP); Shigenobu Nishiguchi, Osaka (JP)

(73) Assignees: THE UNIVERSITY OF TOKYO, Tokyo (JP); TOWA PHARMACEUTICAL CO. LTD., Osaka (JP)

( * ) Notice: Subject to any disclaimer, the term of this patent is extended or adjusted under 35 U.S.C. 154(b) by 0 days.

(21) Appl. No.: 16/381,879

(22) Filed: Apr. 11, 2019

(65) Prior Publication Data

US 2019/0232266 A1    Aug. 1, 2019

Related U.S. Application Data

(62) Division of application No. 15/539,849, filed as application No. PCT/JP2015/086163 on Dec. 25, 2015, now Pat. No. 10,307,748.

(30) Foreign Application Priority Data

Dec. 26, 2014 (JP) ................. 2014-264317

(51) Int. Cl.
*B01J 23/745*   (2006.01)
*B01J 31/22*    (2006.01)
(Continued)

(52) U.S. Cl.
CPC ......... *B01J 31/2243* (2013.01); *B01J 23/745* (2013.01); *B01J 31/00* (2013.01); *C07B 53/00* (2013.01); *C07C 251/24* (2013.01); *C07D 401/12* (2013.01); *C07D 471/04* (2013.01); *C07F 15/025* (2013.01); *B01J 2231/763* (2013.01); *B01J 2531/0205* (2013.01); *B01J 2531/0216* (2013.01);
(Continued)

(58) Field of Classification Search
CPC ................................... B01J 31/2243
See application file for complete search history.

(56) References Cited

U.S. PATENT DOCUMENTS 5,693,818 A   12/1997  Von Unge
5,948,789 A    9/1999  Larsson et al.
(Continued)

FOREIGN PATENT DOCUMENTS

EP   3239146 A1    11/2017
JP   H07509499 A   10/1995
(Continued)

OTHER PUBLICATIONS

Legros et al. I, "Investigations on the, etc.," Chem. Eur. J, 11, 1086-1092. (Year: 2005).*
(Continued)

*Primary Examiner* — Patricia L Morris
(74) *Attorney, Agent, or Firm* — Cantor Colburn LLP

(57) ABSTRACT

A highly pure optically active proton pump inhibitor compound can be produced safely and inexpensively in a high yield and enantioselectivity by a method of producing an optically active sulfoxide of Formula 2 or a salt thereof, comprising oxidizing a sulfide of Formula 1 or a salt thereof with hydrogen peroxide using an iron salt in the presence of a chiral ligand of Formula 3; wherein A is CH or N; $R^1$ is hydrogen atom, an alkyl optionally substituted by halogen(s), or an alkoxy optionally substituted by halogen(s); one to three $R^2$ may exist, and each of $R^2$ is independently an alkyl, a dialkylamino, or an alkoxy optionally substituted by halogen(s) or alkoxy(s); each of $R^3$ is independently hydrogen atom, a halogen, cyano or the like; $R^4$ is a tertiary alkyl; and * and ** represent respectively R configuration or S configuration.

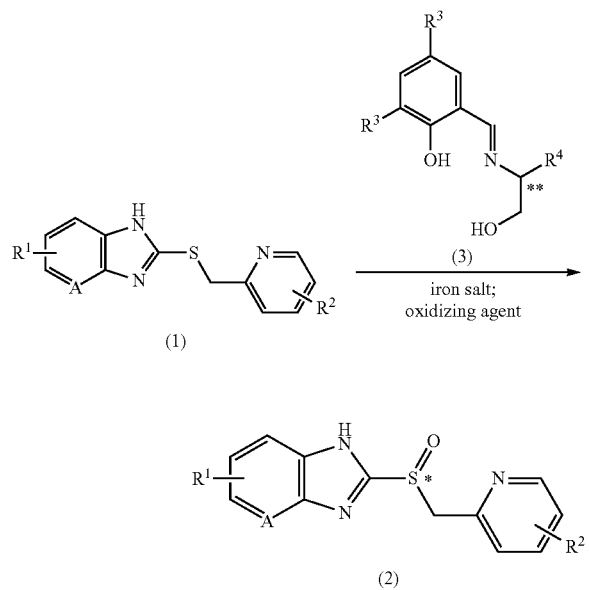

2 Claims, No Drawings

(51) Int. Cl.
*C07D 401/12* (2006.01)
*C07C 251/24* (2006.01)
*C07B 53/00* (2006.01)
*B01J 31/00* (2006.01)
*C07D 471/04* (2006.01)
*C07F 15/02* (2006.01)

(52) U.S. Cl.
CPC .... *B01J 2531/0244* (2013.01); *B01J 2531/0288* (2013.01); *B01J 2531/842* (2013.01); *C07B 2200/07* (2013.01)

(56) References Cited

U.S. PATENT DOCUMENTS

| | | |
|---|---|---|
| 8,889,873 B2 | 11/2014 | Mohar et al. |
| 2003/0171591 A1 | 9/2003 | Hashimoto et al. |
| 2005/0288334 A1 | 12/2005 | Kohl et al. |
| 2006/0281782 A1 | 12/2006 | Cohen et al. |
| 2009/0203911 A1 | 8/2009 | Miyazawa et al. |
| 2009/0292120 A1 | 11/2009 | Ueda et al. |
| 2018/0008971 A1 | 1/2018 | Nakamura et al. |

FOREIGN PATENT DOCUMENTS

| | | |
|---|---|---|
| JP | H10504290 A | 4/1998 |
| JP | 2006516261 A | 6/2006 |
| JP | 2006523201 A | 10/2006 |
| WO | 2001083473 A1 | 11/2001 |
| WO | 2003089408 A2 | 10/2003 |
| WO | 2006112442 A1 | 10/2006 |
| WO | 2008047681 A1 | 4/2008 |
| WO | 2010043601 A1 | 4/2010 |
| WO | 2016104668 A1 | 6/2016 |

OTHER PUBLICATIONS

Korte et al., Asymmetic Synthesis, etc., Synlett. No. 13., 2397-2399. (Year: 2004).*
Bühler, et al., "Chiral Sulfoxides as Metabolites of 2-Thioimidazole-Based p38α Mitogen-Activated Protein Kinase Inhibitors: Enantioselective Synthesis and Biological Evaluation," Journal of Medicinal Chemistry; 2011, vol. 54, No. 9, pp. 3283-3297.
Cotton, et al., "Asymmetric synthesis of esomeprazole," Tetrahedron: Asymmetry; Sep. 22, 2000, vol. 11, pp. 3819-3825.
Extended European Search Report; Application No. EP 15 87 3236 (PCT/JP2015086163); Date of Completion of the Search: Apr. 10, 2018; dated May 2, 2018; 7 pages.
International Preliminary Report on Patentability (English Translation); International Application No. PCT/JP2015/086163; International Filing Date: Dec. 25, 2015; Date of Issuance of this Report: Jun. 27, 2017; 10 Pages.
International Search Report; International Application No. PCT/JP2015/086163; International Filing Date: Dec. 25, 2015; dated Feb. 2, 2016; 3 pages.
Kelly, Pádraig, et al., "Asymmetric Synthesis of Aryl Benzyl Sulfoxides by Vanadium-Catalysed Oxidation: A Combination of Enantioselective Sulfide Oxidation and Kinetic Resolution in Sulfoxide Oxidation," European Journal of Organic Chemistry; 2006, vol. 19, pp. 4500-4509.
Legros et al., "Investigations on the Iron-Catalyzed Asymmetric Sulfide Oxidation," Chemistry—A European Journal; 2005, vol. 11, No. 4, pp. 1086-1092.
Legros et al., "Highly Enantioselective Iron-Catalyzed Sulfide Oxidation with Aqueous Hydrogen Peroxide under Simple Reaction Conditions," Angewandte Chemie International Edition; 2004, vol. 43, No. 32, pp. 4225-4228.
Legros et al., "Iron-Catalyzed Asymmetric Sulfide Oxidation with Aqueous Hydrogen Peroxide," Angewandte Chemie, International Edition; 2003, vol. 42, No. 44, pp. 5487-5489.
Legros, et al, "Applications of Catalytic Asymmetric Sulfide Oxidations to the Syntheses of Biologically Active Sulfoxides," Adv. Synth. Catal.; 2005, vol. 347, pp. 19-31.
Nishiguchi, et al., "Synthesis of Esomeprazole and Related Proton Pump Inhibitors through Iron-Catalyzed Enantioselective Sulfoxidation," ACS Catal., Just Accepted Manuscript; Publication Date (Web): Aug. 29, 2018, pp. 1-7.
O'Mahony, et al., "Investigation of steric and electronic effects in the copper-catalysed asymmetric oxidation of sulfides," Tetrahedron; 2013, vol. 69, No. 47, pp. 10168-10184.
O'Mahony, et al., "Copper-Catalyzed Asymmetric Oxidation of Sulfides," The Journal of Organic Chemistry; 2012, vol. 77, No. 7, pp. 3288-3296.
Ternois, et al., "Asymmetric synthesis of modafinil and its derivatives by enantioselective oxidation of thioethers: comparison of various methods including synthesis in ionic liquids," Tetrahedron: Asymmetry; 2007, vol. 18, pp. 2959-2964.
Thakur et al, "WO3-30% H2O2-cinchona alkaloids: a new heterogeneous catalytic system for the asymmetric oxidation of sulfides and the kinetic resolution of racemic sulfoxides," Tetrahedron: Asymmetry, 2003, 14, pp. 407-410.
Toru et al., "Asymmetric Synthesis of Chiral Sulfoxides," Organosulfur Chemistry in Assymmetric Synthesis; Wiley-VCH Verlag GmbH & Co. KGaA; 208, pp. 1-29.
Written Opinion (English Translation); International Application No. PCT/JP2015/086163; International Filing Date: Dec. 25, 2015; dated Feb. 2, 2016; 9 pages.
Hinch et al. "Effective Asymmetric Oxidation of Enones and Alkyl Aryl Sulfides," Journal of Molecular Catalysis, No. 251, (2006), pp. 123-128.
Bühler, et al.,"Chiral Sulfoxides as Metabolites of 2-Thioimidazole-Based p38a Mitogen-Activated Protein Kinase Inhibitors: Enantioselective Synthesis and Biological Evaluation," (2011), Reference 4, pp. S1-S74.

* cited by examiner

METHOD OF PRODUCING PROTON PUMP INHIBITOR COMPOUND HAVING OPTICAL ACTIVITY

CROSS REFERENCE TO RELATED APPLICATIONS

This application is a Divisional application of U.S. application Ser. No. 15/539,849 filed Jun. 26, 2017, which is a U.S. National Stage Application of PCT/JP2015/086163, filed Dec. 25, 2015, which claims priority to Japanese Application No. 2014-264317, filed Dec. 26, 2014, all of which are incorporated by reference in their entirety.

TECHNICAL FIELD

The present invention relates to a process of producing an optically active proton pump inhibitor compound. More specifically, the present invention relates to a method of producing an optically active proton pump inhibitor compound comprising asymmetric oxidation using an iron salt in the presence of a chiral ligand.

BACKGROUND ART

Proton pump inhibitor is a drug that acts on proton pumps in parietal cells in stomach, and inhibits secretion of gastric acid. Proton pump inhibitor is useful for treating gastric ulcer, duodenal ulcer, anastomotic ulcer, reflux esophagitis, non-erosive gastroesophageal reflux disease or Zollinger-Ellison syndrome, and for sterilization supplement for *Helicobacter pylori* in gastric ulcer, duodenal ulcer, gastric MALT lymphoma, idiopathic thrombocytopenic purpura, remnant stomach after endoscopic submucosal dissection for early gastric cancer, or *Helicobacter pylori* gastritis, and the like. As a proton pump inhibitor compound, a benzimidazole-type or imidazopyridine-type compound or the like are known, as represented by, for example, omeprazole, esomeprazole, lansoprazole, rabeprazole, tenatoprazole, pantoprazole, reminoprazole, dexlansoprazole, which are shown below. The terms "proton pump inhibitor compound" and "benzimidazole-type or imidazopyridine-type compound" as used herein, include either a neutral form or a salt form, or both forms.

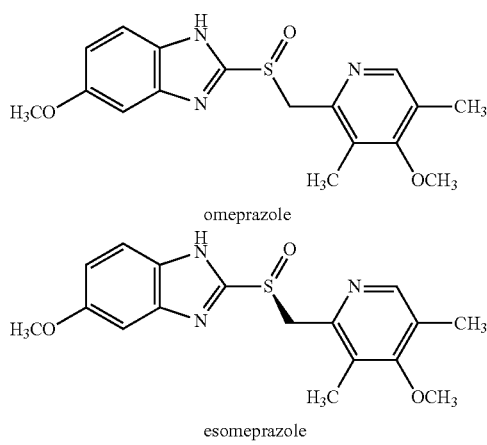

omeprazole esomeprazole

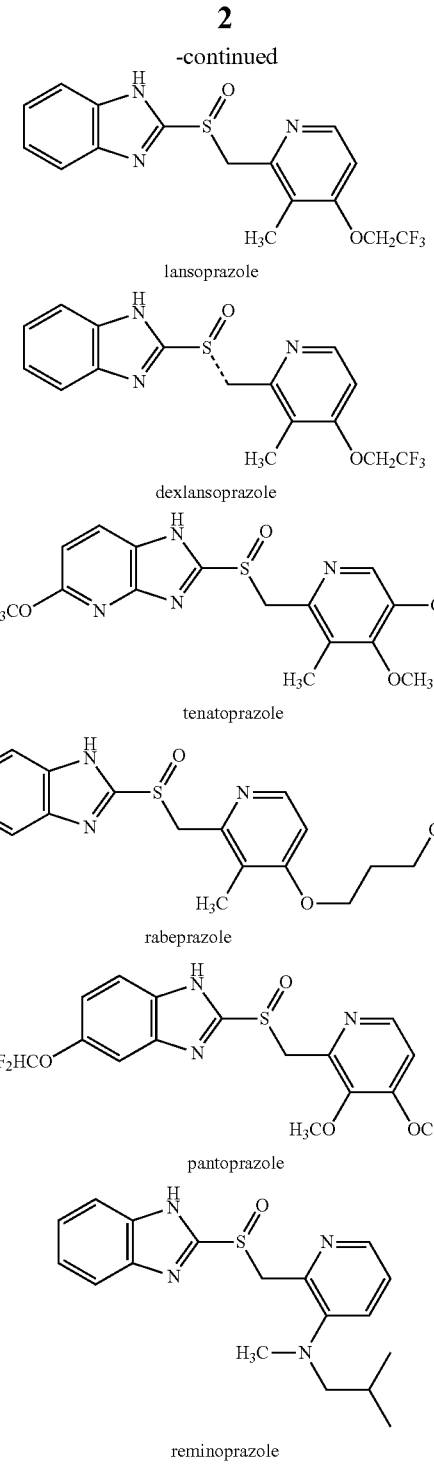

lansoprazole dexlansoprazole tenatoprazole rabeprazole pantoprazole reminoprazole The proton pump inhibitor compound may exist as S-form, R-form or a racemate, based on the conformational structure of the sulfur atom in the sulfoxide, as a common characteristic of their structure. As for omeprazole, its racemate is called omeprazole, and its S-form is called esomeprazole, both of which are commercially available. Esomeprazole has smaller inter-individual variation in pharmacokinetics and pharmacodynamic effects as compared with omeprazole, and was developed as a drug that exerts more clinical effects beyond omeprazole. Thus, since an optically active proton pump inhibitor compound was expected to have better clinical effects than its racemic form, a method of producing its optically active compound efficiently had been desired.

Patent Literature 1 discloses a method of producing esomeprazole by preparing an ester of a racemic omeprazole with an optically active acid, followed by separating the obtained diastereomers. However, the method requires multi-steps, and the other optical isomer is discarded. Therefore, this method is not preferable.

Non-Patent Literature 1 and Patent Literature 2 disclose a method of producing optically active esomeprazole by asymmetric oxidation. The authors reported that enantioselectivity of 94% ee or more was obtained by this method using titanium as a catalyst, and diethyl (S, S)-tartrate as a chiral ligand, and cumene hydroperoxide as an oxidant. However, they describe that the asymmetric oxidation reaction using this titanium catalyst was not reproducible. Particularly, while asymmetric oxidation using a catalyst amount of 4 mol % proceeded with 91% ee on a small scale, this results could not be reproduced with the same catalyst amount on a larger scale, and a catalyst amount of for example 30 mol % was required for asymmetric oxidation. Accordingly, the method of Non-Patent Literature 1 and Patent Literature 2 have problems that a large amount of the catalyst and the chiral ligand are necessary on an industrial scale, and furthermore, these catalysts, chiral ligands and oxidants are expensive and not easy to handle.

Patent Literatures 3 and 4 disclose examples in which the method of Non-Patent Literature 1 was applied to other proton pump inhibitor compounds such as lansoprazole and the like. Patent Literature 5 discloses a method of producing esomeprazole using optically active methyl mandelate instead of a tartarate derivative in the method of Non-Patent Literature 1. In the methods of Patent Literatures 3 to 5, a large amount of titanium catalyst is used as in the method of Non-Patent Literature 1.

Patent Literature 6 discloses a method of producing an optically active form of pantoprazole and the like, using zirconium or hafnium instead of titanium catalyst in the method of Non-Patent Literature 1. However, the method has problems that the catalysts, chiral ligands and oxidants are expensive and not easy to handle.

Patent Literature 7 discloses a method of producing an optically active form of tenatoprazole using tungsten or vanadium as a catalyst, an alkaloid derivative or an imine derivative as a chiral ligand and hydrogen peroxide as an oxidant. It describes for example, in Example 1, that the desired optical isomer was obtained in 70% yield and 90% ee, after the reaction, extraction and concentration under a reduced pressure. However, the contents of the sulfone compound and the unreacted sulfide compound are not described, which should also be present after only simple extraction. Moreover, the yield of the compound obtained after recrystallization is not described at all. Therefore, the above yield is considered to be a numerical value including impurities which is unreliable and the yield is not considered to be so high. Furthermore, the method of Patent Literature 7 has problems that these catalysts and chiral ligands are expensive and not easy to handle as in Patent Literature 6.

Non-Patent Literature 2 discloses that an optically active form of lansoprazole was produced using a tungsten catalyst, an alkaloid derivative as a chiral ligand, and hydrogen peroxide as an oxidant. However, the method has problems that the catalysts and chiral ligands are expensive and not easy to handle.

Patent Literature 8 discloses a method of producing esomeprazole using a manganese salt as a catalyst, salen derivative as a chiral ligand and hydrogen peroxide as an oxidant. However, the yield is 6 to 62% and the enantioselectivity is 3 to 62% ee, which are not satisfactory for a method of producing an optically active compound. Furthermore, when manganese was replaced by iron as described in Example 37, the yield decreased to 17% and the enantioselectivity to 18% ee. A person skilled in the art who reads Patent Literature 8 would understand that iron is inferior to manganese as a catalyst and is not a preferable catalyst in the production of proton pump inhibitors having similar benzimidazole-type and imidazopyridine-type structure including esomeprazole.

A method of asymmetric oxidation of a sulfide using an iron catalyst is described in Non-Patent Literatures 3 and 4. This method uses a specific imine compound as a chiral ligand, iron (III) acetylacetonate as an iron salt, and hydrogen peroxide in water as an oxidant. As shown in Table 3 of Non-Patent Literature 4, the yield is 36 to 78% and the enantioselectivity is 23 to 96% ee when additives were used. From the results, it seems that the yield and enantioselectivity are largely dependent on the structure of the starting material sulfide. Also, the sulfides used are mainly limited to those having an aromatic hydrocarbon group and an alkyl group. Therefore, it is impossible for a person skilled in the art to predict the yield and enantioselectivity for the asymmetrical oxidation of a compound having a heterocyclic ring under these conditions.

CITATION LIST

Patent Literature

Patent Literature 1: JP H07-509499
Patent Literature 2: JP H10-504290
Patent Literature 3: WO 01/83473
Patent Literature 4: WO 2008/047681
Patent Literature 5: WO 03/089408
Patent Literature 6: JP 2006-516261
Patent Literature 7: JP 2006-523201
Patent Literature 8: WO 2010/043601

Non-Patent Literature

Non-Patent Literature 1: Tetrahedron: Asymmetry, 2000, 11, 3819-3825
Non-Patent Literature 2: Tetrahedron: Asymmetry, 2003, 14, 407-410
Non-Patent Literature 3: Angew. Chem. Int. Ed., 2004, 43, 4225-4228
Non-Patent Literature 4: Chem. Eur. J., 2005, 11, 1086-1092

SUMMARY OF THE INVENTION

Technical Problem

The purpose of the present invention is to provide a method of producing a highly pure optically active proton pump inhibitor compound safely and inexpensively in a high yield and enantioselectivity.

Solution to the Problem

The present inventors have done intensive research to solve the above problem, and have found that by iron-catalyzed asymmetric oxidation of a sulfide that is the starting material for a proton pump inhibitor compound, an optically active proton pump inhibitor compound can be produced in a high yield and high enantioselectivity which had not been achieved so far. Thus, the present inventors have accomplished the present invention, which is as follows.

[1] A method of producing an optically active sulfoxide of Formula 2 or a salt thereof, comprising oxidizing a sulfide of Formula 1 or a salt thereof,

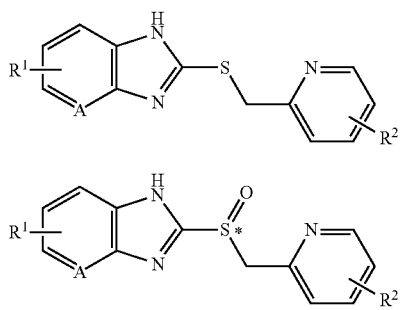

wherein A is CH or N; $R^1$ is a hydrogen atom, an alkyl optionally substituted by halogen(s), or an alkoxy optionally substituted by halogen(s); one to three $R^2$ may exist, and each of $R^2$ is independently an alkyl, a dialkylamino, or an alkoxy optionally substituted by halogen(s) or alkoxy(s); and * represents R configuration or S configuration, with hydrogen peroxide using an iron salt in the presence of a chiral ligand of Formula 3:

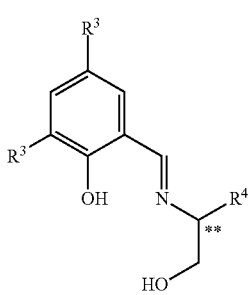

wherein each of $R^3$ is independently hydrogen atom, a halogen, cyano, an alkylsulfonyl, an arylsulfonyl, an alkanoyl, an alkoxycarbonyl, nitro, an alkyl optionally substituted by halogen(s), or an alkoxy optionally substituted by halogen(s); $R^4$ is a tertiary alkyl; and ** represents R configuration or S configuration.

[2] The method according to [1], wherein the oxidation reaction is performed after adding an optionally substituted benzoic acid or a salt thereof.

[3] The method according to [1] or [2], wherein the oxidation reaction of a sulfide of Formula 1 or a salt thereof is performed after adding another sulfide or a sulfoxide or sulfone corresponding to another sulfide to the reaction system.

[4] The method according to any one of [1] to [3], wherein both of $R^3$ are chlorine atoms, and $R^4$ is t-butyl.

[5] The method according to any one of [1] to [4], wherein the optically active sulfoxide of Formula 2 is an optically active form of omeprazole, lansoprazole, rabeprazole, tenatoprazole, pantoprazole or reminoprazole.

[6] An iron complex coordinated with a chiral ligand of Formula 4:

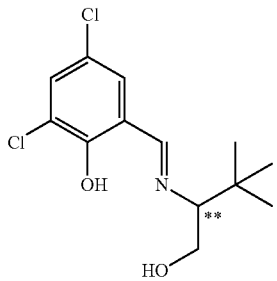

wherein ** represents R configuration or S configuration.

Advantageous Effects of the Invention

By a production method of the present invention using an iron complex, a highly pure optically active proton pump inhibitor compound can be produced safely and inexpensively in a high yield and enantioselectivity. Also, since the method of the present invention uses inexpensive and safe hydrogen peroxide as an oxidant, it is advantageous over previous methods that use cumene hydroperoxide and the like, because only water is formed after the reaction, and treatment of by-products is unnecessary.

DESCRIPTION OF THE INVENTION

The present invention provides a method of producing an optically active sulfoxide of Formula 2 or a salt thereof, comprising oxidizing a sulfide of Formula 1 or a salt thereof, with hydrogen peroxide using an iron salt in the presence of a chiral ligand of Formula 3.

1. Sulfide of Formula 1 and Optically Active Sulfoxide of Formula 2

"Alkyl optionally substituted by halogen(s)" in $R^1$ includes, for example, a linear or branched $C_1$-$C_5$ alkyl optionally substituted by one or more halogens selected from fluorine atom, chlorine atom and bromine atom, and the like.

"Alkoxy optionally substituted by halogen(s)" in $R^1$ includes, for example, a linear or branched $C_1$-$C_5$ alkoxy optionally substituted by one or more halogens selected from fluorine atom, chlorine atom and bromine atom, and the like, preferably methoxy optionally substituted by one or two fluorine atoms, and the like.

"Alkyl" in $R^2$ includes, for example, a straight or branched $C_1$-$C_5$ alkyl and the like, preferably methyl and the like.

"Dialkylamino" in $R^2$ includes, for example, an amino substituted by two straight or branched $C_1$-$C_5$ alkyls and the like, preferably methylisobutylamino and the like.

"Alkoxy optionally substituted by halogen(s) or alkoxy(s)" in $R^2$ includes, for example, a straight or branched $C_1$-$C_5$ alkoxy optionally substituted by one or more halogens selected from fluorine atom, chlorine atom and bromine atom, or by a straight or branched $C_1$-$C_5$ alkoxy and the like, preferably methoxy, 3-methoxypropoxy, 2,2,2-trifluoroethoxy and the like.

Asterisk "*" in an optically active sulfoxide of Formula 2 represents R configuration or S configuration. The desired configuration of an optically active sulfoxide is determined according to its biological activity, but it is preferably the S configuration.

Preferable examples of an optically active sulfoxide of Formula 2 include, for example, an optically active form of omeprazole, lansoprazole, rabeprazole, tenatoprazole, pantoprazole or reminoprazole, and particularly preferred is esomeprazole, the optically active form of omeprazole having S configuration.

"Salt of a sulfide of Formula 1" and "salt of an optically active sulfoxide of Formula 2" include, for example, an alkali metal salt, an alkaline earth metal salt, an ammonium salt and the like. Specific examples of the salts include a lithium salt, a sodium salt, a potassium salt, a magnesium salt, a calcium salt, an ammonium salt and the like. Preferable salts of an optically active sulfoxide of Formula 2 includes a pharmaceutically acceptable salt.

2. Chiral Ligand of Formula 3

"Halogen" in $R^3$ includes, for example, fluorine atom, chlorine atom, bromine atom, iodine atom and the like, preferably fluorine atom, chlorine atom and bromine atom, more preferably chlorine atom and bromine atom, and particularly preferably chlorine atom.

"Alkylsulfonyl" in $R^3$ includes, for example, a straight or branched $C_1$-$C_5$ alkylsulfonyl and the like, preferably methylsulfonyl, ethylsulfonyl and the like.

"Arylsulfonyl" in $R^3$ includes, for example, a $C_6$-$C_{10}$ arylsulfonyl and the like, preferably phenylsulfonyl and the like.

"Alkanoyl" in $R^3$ includes, for example, a straight or branched $C_1$-$C_5$ alkanoyl and the like, preferably acetyl and the like.

"Alkoxycarbonyl" in $R^3$ includes, for example, a straight or branched $C_1$-$C_5$ alkoxycarbonyl and the like, preferably methoxycarbonyl, ethoxycarbonyl and the like.

"Alkyl optionally substituted by halogen(s)" in $R^3$ includes, for example, a straight or branched $C_1$-$C_5$ alkyl optionally substituted by one or more halogens selected from fluorine atom, chlorine atom and bromine atom, and the like, preferably perfluoroalkyl and the like, more preferably trifluoromethyl and the like.

"Alkoxy optionally substituted by halogen(s)" in $R^3$ includes, for example, a straight or branched $C_1$-$C_5$ alkoxy optionally substituted by one or more halogens selected from fluorine atom, chlorine atom and bromine atom, and the like, preferably trifluoromethoxy, pentafluoroethoxy and the like.

Preferable examples of $R^3$ include hydrogen atom, fluorine atom, chlorine atom, bromine atom, iodine atom, cyano, methylsulfonyl, phenylsulfonyl, acetyl, methoxycarbonyl, nitro, trifluoromethyl and the like. More preferable is hydrogen atom, chlorine atom, bromine atom, iodine atom, methylsulfonyl, nitro, trifluoromethyl and the like, further preferable is chlorine atom, bromine atom, iodine atom and the like, and particularly preferable is chlorine atom. Two $R^3$s may be the same or different, and preferably are the same.

"Tertiary alkyl" in $R^4$ includes, for example, t-butyl, t-pentyl, t-hexyl and the like, preferably t-butyl.

Asterisks "**" in the chiral ligand of Formula 3 represents R configuration or S configuration. R configuration or S configuration of the chiral ligand may be selected according to the configuration of the desired optically active sulfoxide. Preferred is the S configuration. By performing the asymmetric oxidation using a chiral ligand of Formula 3 having S configuration, an optically active sulfoxide of Formula 2 having S configuration can be produced.

Particularly preferred chiral ligands include the chiral ligand of Formula 4.

3. Production Method

A production method of the present invention may be carried out, for example, by reacting a chiral ligand of Formula 3 with an iron salt to form an iron complex coordinated with the chiral ligand of Formula 3, followed by adding a sulfide of Formula 1 or a salt thereof, and adding hydrogen peroxide.

As "iron salt" used in the production method of the present invention, any iron salt may be used as long as it can be coordinated with a chiral ligand of Formula 3 in the reaction system. Iron in the iron salt may be divalent or trivalent. Specific examples of an iron salt include, for example, iron(III) acetylacetonate, iron(II) chloride, iron (III) chloride, iron(II) bromide, iron(III) bromide, iron(II) acetate, iron(II) trifluoromethanesulfonate, iron(II) tetrafluoroborate, iron(II) perchlorate, iron(III) perchlorate, iron (II) sulfate, iron(II) di[bis(trifluoromethylsulfonyl)imide] and the like. Preferred iron salts include iron(III) acetylacetonate and the like.

In a production method of the present invention, the amount of an iron salt includes, for example, about 0.1 to about 20 mol %, preferably about 2 to about 15 mol %, more preferably about 5 to about 12 mol %, based on the amount of a sulfide of Formula 1. Unlike the titanium catalyst described in Non-Patent Literature 1 and the like, it is unnecessary to increase the number of equivalent of an iron salt even if production scale is larger.

The amount of a chiral ligand of Formula 3 includes about 1 to about 5 equivalents, preferably about 1.05 to about 3 equivalents, more preferably about 1.1 to about 2 equivalents, and further preferably about 1.1 to about 1.5 equivalents, based on the amount of an iron salt.

A chiral ligand of Formula 3 may be mixed with an iron salt in a reaction solvent, for example, at a temperature of about 0 to about 40° C. or the like, preferably about 10 to about 30° C., for example, for about 10 minutes to about 24 hours, preferably about 20 minutes to about 5 hours, more preferably about 30 minutes to about 1 hour, to form an iron complex coordinated with a chiral ligand of Formula 3.

As "hydrogen peroxide" used in a production method of the present invention, for example, commercially available 30 to 50% hydrogen peroxide in water and the like may be suitably used. In addition, for example, urea-hydrogen peroxide (urea-hydrogen peroxide adduct, abbreviated to UHP) in which hydrogen peroxide is included in urea, may also be used. The amount of hydrogen peroxide includes, for example, about 1.1 to about 5 equivalents, preferably about 1.2 to about 3 equivalents, more preferably about 1.5 to about 2.5 equivalents, further preferably about 1.8 to about 2.3 equivalents, based on the amount of a sulfide of Formula 1.

"Reaction solvent" includes, for example, an ester such as ethyl acetate, isopropyl acetate and the like, a halogenated hydrocarbon such as methylene chloride, chloroform, 1,2-dichloroethane and the like, an alcohol such as methanol, ethanol, ethylene glycol and the like, a nitrile such as acetonitrile and the like, a ketone such as acetone, methyl isobutyl ketone and the like, an ether such as t-butyl methyl ether and the like, an amide such as dimethylformamide, dimethylacetamide and the like, and a mixed solvent of one of these solvents and an aromatic hydrocarbon such as toluene, anisole and the like, and a mixed solvent of these solvents, and the like. Further, these solvents may be mixed with water. Preferred reaction solvent includes an ester such as ethyl acetate, isopropyl acetate and the like, a mixed solvent of an alcohol such as methanol, ethanol and the like and an aromatic hydrocarbon such as toluene and the like, and the like, to give higher enantioselectivity.

The amount of a reaction solvent includes, for example, about 4 to about 15 times by weight, preferably about 5 to about 10 times by weight, relative to the weight of a sulfide of Formula 1.

"Reaction temperature" includes, for example, about −80 to about 30° C. and the like, preferably about −30 to about 15° C., more preferably about −15 to about 5° C. Since enantioselectivity tends to decrease at a temperature above 15° C., it is preferable to react at a temperature below 15° C.

"Reaction time" includes, for example, about 1 to about 50 hours and the like, preferably about 2 to about 24 hours in terms of operation. It is preferable to monitor the reaction progress by HPLC or the like, and to stop the reaction at the optimal time. A sulfide is oxidized to the desired sulfoxide, but as a side reaction the sulfoxide may be further oxidized to form a sulfone. In the case of using an asymmetric ligand of Formula 3 having S configuration, S-sulfoxide is formed selectively over R-sulfoxide. Conversely, oxidation of R-sulfoxide to a sulfone as a side reaction proceeds more preferentially than that of S-sulfoxide. Therefore, this second oxidation also increases the enantioselectivity.

In a production method of the present invention, by adding an optionally substituted benzoic acid or a salt thereof, followed by oxidation reaction, enantioselectivity may be further improved. An optionally substituted benzoic acid or a salt thereof may be added after formation of an iron complex coordinated with a chiral ligand of Formula 3.

A substituent in "optionally substituted benzoic acid" includes, for example, an aryl such as phenyl and the like, an alkoxy such as methoxy and the like, nitro, a halogen such as fluorine atom, chlorine atom, bromine atom and the like, an alkyl such as methyl, ethyl and the like, a dialkylamino such as dimethylamino and the like, and the like. Preferred substituents include dimethylamino, methoxy and the like. One or more substituents may exist, and the preferred substitution position includes 4-position. Preferred examples of "optionally substituted benzoic acid" include 4-dimethylaminobenzoic acid, 4-methoxybenzoic acid and the like.

A salt in "optionally substituted benzoic acid" includes, for example, a lithium salt, a sodium salt, a potassium salt, a cesium salt, a tetrabutylammonium salt and the like. A lithium salt is preferable in terms of enantioselectivity and stirring feasibility in the reaction system.

The amount of an optionally substituted benzoic acid or a salt thereof includes, for example, about 30 to about 200 mol %, preferably about 50 to about 150 mol %, more preferably about 80 to about 120 mol %, based on the amount of an iron salt.

In a production method of the present invention, enantioselectivity of a formed sulfoxide is slightly low immediately after the oxidation reaction starts, but as the oxidation reaction proceeds, enantioselectivity increases. The present inventors considered that this phenomenon occurs because the formed sulfoxide contributes to the subsequent oxidation reaction to some extent. Accordingly, prior to the oxidation reaction of a sulfide of Formula 1, another sulfide or a sulfoxide or sulfone corresponding to another sulfide was added to the reaction system in advance, and the oxidation reaction of a sulfide of Formula 1 was conducted. As a result, the inventors have found that the enantioselectivity was further improved.

"Another sulfide" to be added includes, for example, a sulfide represented by Formula: $R^5$—S—$R^6$ or the like, wherein $R^5$ and $R^6$ are independently an optionally substituted alkyl, an optionally substituted aryl, or an optionally substituted heteroaryl. An alkyl in $R^5$ and $R^6$ includes, for example, a straight or branched $C_1$-$C_5$ alkyl and the like, and the specific examples include methyl, ethyl, propyl, butyl, pentyl and the like. A substituent in the substituted alkyl includes, for example, a $C_6$-$C_{10}$ aryl, a 5- or 6-membered heteroaryl and the like, and the specific examples include phenyl, naphthyl, pyridyl, pyrimidinyl, imidazolyl, furyl, oxazolyl and the like. An aryl in $R^5$ and $R^6$ includes, for example, a $C_6$-$C_{10}$ aryl and the like, and the specific examples include phenyl, naphthyl and the like. A substituent in the substituted aryl includes, for example, an alkyl, an alkoxy, a halogen, nitro, an alkanoyl, an alkoxycarbonyl, an aryl, a heteroaryl and the like. A heteroaryl in $R^5$ and $R^6$ includes, for example, a 5- or 6-membered monocyclic heteroaryl, a bicyclic heteroaryl and the like, and the specific examples include pyridyl, pyrimidinyl, imidazolyl, furyl, oxazolyl, benzimidazolyl, quinoxalyl and the like. A substituent in the substituted heteroaryl includes, for example, an alkyl, an alkoxy, a halogen, nitro, an alkanoyl, an alkoxycarbonyl, an aryl, a heteroaryl and the like.

Specific examples of another sulfide include dimethyl sulfide, diethyl sulfide, dipropyl sulfide, dibutyl sulfide, thioanisole, ethyl phenyl sulfide, diphenyl sulfide, benzyl phenyl sulfide, benzimidazolyl pyridylmethyl sulfide and the like, more preferably thioanisole, ethyl phenyl sulfide, diphenyl sulfide, benzyl phenyl sulfide, benzimidazolyl pyridylmethyl sulfide and the like, and particularly preferably diphenyl sulfide, benzyl phenyl sulfide, benzimidazolyl pyridylmethyl sulfide and the like. Use of a bulky sulfide further improves enantioselectivity. The amount of another sulfide includes, for example, about 2 to about 30 mol %, preferably about 5 to about 15 mol %, based on the amount of a sulfide of Formula 1.

It is preferable that after formation of an iron complex coordinated with a chiral ligand of Formula 3, another sulfide is added, and hydrogen peroxide is added, and then the sulfide of Formula 1 is added to perform the reaction.

Instead of adding another sulfide, a sulfoxide or sulfone corresponding to another sulfide may be added after formation of an iron complex coordinated with a chiral ligand of Formula 3.

4. Preparation of an Optically Active Proton Pump Inhibitor Compound

After completion of the oxidation reaction, the reaction may be stopped by decomposing hydrogen peroxide by adding an aqueous solution of a reducing agent. A reducing agent includes, for example, a thiosulfate salt such as sodium thiosulfate and the like, a sulfite salt such as sodium sulfite and the like, and the like. When an aqueous solution of a reducing agent is added, the iron used is dissolved in the aqueous solution. Following the above procedure, the product may be extracted into an organic layer and then purified according to a conventional method. Since an optically active sulfoxide of Formula 2 is soluble in a basic water, the sulfoxide may be dissolved in a basic water having a pH of 8 or more, and washed with a hydrophobic organic solvent, and then after addition of an acid to the aqueous layer, the sulfoxide may be extracted into an organic layer. Through this procedure, the by-product sulfone and the unreacted sulfide can be removed conveniently. Thereafter, the sulfoxide may be purified by recrystallization or the like. In addition, an optically active sulfoxide of Formula 2 may be converted into its salt according to a conventional method if necessary.

5. Use of an Optically Active Proton Pump Inhibitor Compound

A pharmaceutical composition comprising as an active ingredient an appropriate amount of an optically active proton pump inhibitor compound produced by a production method of the present invention, may be prepared in the same manner as those of its known racemate. The prepared pharmaceutical composition is a drug that acts on proton pumps in parietal cells in stomach, and inhibits secretion of gastric acid. The pharmaceutical composition is useful for treating gastric ulcer, duodenal ulcer, anastomotic ulcer, reflux esophagitis, non-erosive gastroesophageal reflux disease or Zollinger-Ellison syndrome, and for sterilization supplement for *Helicobacter pylori* in gastric ulcer, duodenal ulcer, gastric MALT lymphoma, idiopathic thrombocytopenic purpura, remnant stomach after endoscopic submucosal dissection for early gastric cancer, or *Helicobacter pylori* gastritis, or the like.

EXAMPLES

Hereinafter, the present invention is further described in more detail with reference to Examples, but the present invention is not limited to these Examples.

Hereinafter, each compound included in the reaction solution is represented by the following abbreviations.
[Sulfide A] 5-methoxy-2-[[(4-methoxy-3,5-dimethyl-2-pyridinyl)methyl]thio]-1H-benzimidazole (starting material)
[S-sulfoxide A] S-sulfoxide of sulfide A (esomeprazole)
[R-sulfoxide A] R-sulfoxide of sulfide A
[Sulfone A] sulfone of sulfide A
[S-dichloro chiral ligand] 2,4-Dichloro-6-[(E)-[[(1S)-1-(hydroxymethyl)-2,2-dimethylpropyl] imino]methyl]-phenol (chiral ligand of Formula 4 having S configuration)

The amount of each compound included in the reaction solution was measured using the following HPLC analysis conditions 1 to 3.

<HPLC Analysis Condition 1>
High performance liquid chromatography was performed using the following parameters.
[Column] Daicel Chiralpak IA (4.6 mm×250 mm, particle size 5 μm)
[Column temperature] 25° C.
[Mobile phase] t-Butyl methyl ether:ethyl acetate:ethanol:diethylamine:trifluoroacetic acid=
60:40:5:0.1:0.1
[Flow rate] 1.0 mL/min
[Detection wavelength] 299 nm
[Measurement time] 30 min
[Approximate retention time]
4-dimethylaminobenzoic acid: 3.6 min
S-dichloro chiral ligand: 4.0 min
Sulfone A: 5.5 min
Sulfide A: 6.6 min
R-sulfoxide A: 10.3 min
S-sulfoxide A: 14.6 min <HPLC Analysis Condition 2>
High performance liquid chromatography was performed using the following parameters.
[Column] ZORBAX SB-C8 (4.6 mm×150 mm, particle size 3.5 μm)
[Column temperature] 25° C.
[Mobile phase] mobile phase A: aqueous sodium phosphate solution of pH 7.6; mobile phase B: acetonitrile
(Aqueous sodium phosphate solution of pH 7.6 was prepared by dissolving 2.83 g of disodium hydrogen phosphate $12H_2O$ and 0.21 g of sodium dihydrogen phosphate $2H_2O$ in 1,000 mL of water and adjusting the pH to 7.6 with 1 vol % aqueous phosphoric acid solution.)

The concentration gradient was controlled by changing the mixing ratio of mobile phase A and mobile phase B as follows.

TABLE 1

| Time after injection (min) | Mobile phase A (vol %) | Mobile phase B (vol %) |
| --- | --- | --- |
| 0 to 10 | 75 | 25 |
| 10 to 35 | 75 -> 40 | 25 -> 60 |
| 35 to 45 | 40 | 60 |

[Flow rate] 1.0 mL/min
[Detection wavelength] 280 nm
[Measurement time] 45 min
[Approximate retention time]
(1) Lansoprazole
Sulfone: 20.4 min
Sulfoxide: 22.9 min
Sulfide: 30.5 min
(2) Rabeprazole
Sulfone: 13.7 min
Sulfoxide: 18.3 min
Sulfide: 27.9 min
(3) Pantoprazole
Sulfone: 8.6 min
Sulfoxide: 17.5 min
Sulfide: 28.2 min <HPLC Analysis Condition 3>
High performance liquid chromatography was performed using the following parameters.
[Column] Daicel Chiralpak IC (4.6 mm×250 mm, particle size 5 μm)
[Column temperature] 40° C.
[Mobile phase] 5M aqueous potassium dihydrogen phosphate solution of pH 6.5:methanol:tetrahydrofuran=37:60:3
(5M aqueous potassium dihydrogen phosphate solution of pH 6.5 was prepared by dissolving 0.7 g of potassium dihydrogen phosphate in 1,000 mL of water and adjusting the pH to 6.5 with triethylamine.)
[Flow rate] 1.0 mL/min
[Detection wavelength] 300 nm
[Measurement time] 30 min
[Approximate retention time]
(1) Omeprazole
S-sulfoxide A: 12.5 min
R-sulfoxide A: 15.7 min
(2) Lansoprazole
S-sulfoxide: 8.8 min
R-sulfoxide: 10.6 min
(3) Rabeprazole
S-sulfoxide: 16.2 min
R-sulfoxide: 20.9 min
(4) Pantoprazole
S-sulfoxide: 7.8 min
R-sulfoxide: 8.8 min

Example 1

Production of S-Sulfoxide A (Esomeprazole)

79.3 mg (273 μmol) of S-dichloro chiral ligand and 32.2 mg (91.1 μmol) of iron(III) acetylacetonate were dissolved in 0.6 mL of ethyl acetate at 25° C., and stirred for more than 30 min. To the mixed solution were added 7.8 mg (45.5 μmol) of lithium 4-dimethylaminobenzoate and 0.3 mL of ethyl acetate, and the suspension was stirred for more than 30 min. 0.3 g (911 μmol) of sulfide A and 0.9 mL of ethyl acetate were added and the suspension was stirred for more than 30 min. After the mixture was cooled to −5° C., 186 μL (1.82 mmol) of 30% aqueous hydrogen peroxide solution was added dropwise for 2 min or more. After 4.5 hours, the reaction mixture was analyzed under HPLC analysis condition 1.

<Content> sulfoxide A 88%; sulfone A 11%; sulfide A 0%
<Enantiomer excess of sulfoxide A> 98% ee

Examples 2 to 8

Investigation of Reaction Solvent

Asymmetric oxidation reaction was performed in the same manner as in Example 1 except for using each reaction solvent shown in Table 2 instead of ethyl acetate. The results of the reaction mixture analysis under HPLC analysis condition 1 at the reaction time in Table 2, are shown in Table 2.

TABLE 2

| | Reaction solvent | Reation time | Sulfoxide A | Sulfone A | Sulfide A | % ee |
|---|---|---|---|---|---|---|
| Example 1 | Ethyl acetate | 4.5 hr | 88 | 11 | 0 | 98 |
| Example 2 | Methylene chloride | 3 hr | 77 | 8 | 15 | 90 |
| Example 3 | Methanol | 20.5 hr | 81 | 14 | 8 | 90 |
| Example 4 | Ethanol | 20.5 hr | 80 | 17 | 17 | 91 |
| Example 5 | Acetonitrile | 20.5 hr | 79 | 20 | 1 | 92 |
| Example 6 | Toluene/Methanol (1:1 (v/v)) | 20.5 hr | 79 | 13 | 9 | 97 |
| Example 7 | Methyl isobutyl ketone | 3.5 hr | 72 | 7 | 21 | 91 |
| Example 8 | t-butyl methyl ether | 4.5 hr | 54 | 9 | 36 | 92 |

Since reaction rate varied depending on the reaction solvent, the analysis time of the reaction mixture was changed. As can be seen from the above results, all reaction solvents gave generally good enantioselectivity. Especially, ethyl acetate and toluene/methanol showed extremely high enantioselectivity.

Examples 9 to 12

Investigation of Reaction Temperature

Asymmetric oxidation reaction was performed at the reaction temperature to the temperature shown in Table 3, in the same manner as in Example 2 except for using 4-dimethylaminobenzoic acid instead of lithium 4-dimethylaminobenzoate. The results of the reaction mixture analysis under HPLC analysis condition 1 at the reaction time in Table 3, are shown in Table 3.

TABLE 3

| | Reaction temperature | Reaction time | Sulfoxide A | Sulfone A | Sulfide A | % ee |
|---|---|---|---|---|---|---|
| Example 9 | −9° C. | 4.5 hr | 78 | 14 | 5 | 94 |
| Example 10 | −5° C. | 3.5 hr | 76 | 15 | 9 | 90 |
| Example 11 | 5° C. | 2.5 hr | 73 | 27 | 1 | 95 |
| Example 12 | 15° C. | 1.5 hr | 76 | 19 | 6 | 82 |

Since reaction rate varied depending on the reaction temperature, the analysis time of the reaction mixture was changed accordingly. As can be seen from the above results, good enantioselectivity was obtained, and selectivity of 90% or more was observed at 5° C. or less.

Example 13

Production of S-Sulfoxide A (Esomeprazole) Using Urea-Hydrogen Peroxide as an Oxidant Asymmetric oxidation reaction was performed in the same manner as in Example 1 except for using solid urea-hydrogen peroxide (171 mg) instead of 30% aqueous hydrogen peroxide solution as an oxidant and using a mixed solvent of ethyl acetate and water (10:1 (v/v)) instead of ethyl acetate. After 6 hours, the reaction mixture was analyzed under HPLC analysis condition 1.

<Content> sulfoxide A 77%; sulfone A 6%; sulfide A 17%
<Enantiomer excess of sulfoxide A> 87% ee

Example 14

Production of S-Sulfoxide A (Esomeprazole)

52.9 mg (182 μmol) of S-dichloro asymmetric ligand and 32.2 mg (91.1 μmol) of iron(III) acetylacetonate were dissolved in 0.6 mL of ethyl acetate at 25° C., and stirred for more than 30 min. To the mixed solution were added 7.8 mg (45.5 μmol) of lithium 4-dimethylaminobenzoate and 0.3 mL of ethyl acetate, and the suspension was stirred for more than 30 min. 0.3 g (911 μmol) of sulfide A and 0.9 mL of ethyl acetate were added and the suspension was stirred for more than 30 min. After the mixture was cooled to −5° C., 186 μL (1.82 mmol) of 30% aqueous hydrogen peroxide solution was added dropwise for more than 2 min. After 4.5 hours, the reaction mixture was analyzed under HPLC analysis condition 1.

<Content> sulfoxide A 83%; sulfone A 15%; sulfide A 2%
<Enantiomer excess of sulfoxide A> 97% ee To the mixture were added 2.8 mL of 8% aqueous sodium hydrogen carbonate solution, 1.4 g of sodium thiosulfate 5$H_2O$ and 1.4 mL of water, and the mixture was heated to 25° C. and stirred. After removing the aqueous layer, the organic layer was washed twice with 1 mL of 8% aqueous sodium hydrogen carbonate solution. The organic layer was analyzed under HPLC analysis condition 1.

<Content> sulfoxide A 86%; sulfone A 14%; sulfide A 0%
<Enantiomer excess of sulfoxide A> 98% ee Then, after treatment by concentration and silica gel column chromatography (eluent: mixed solvent of chloroform and methanol) was conducted to give 0.3 g of the title compound (purity 87%; 98% ee).

$^1$H NMR (400 MHz, $CDCl_3$): δ 8.21 (1H, s), 7.58 (1H, br s), 6.96 (2H, br m), 4.75 (2H, q, —$SOCH_2$—), 3.84 (3H, s), 3.69 (3H, s), 2.23 (3H, s), 2.21 (3H, s)

Example 15

Addition of Dibutyl Sulfide

Asymmetric oxidation reaction was performed basically in the same manner as in Example 1. 16 µL of dibutyl sulfide (91.1 µmol) was added prior to addition of sulfide A, and the mixture was cooled to −5° C. 186 µL (1.82 mmol) of 30% aqueous hydrogen peroxide solution was added dropwise, and the mixture was stirred for 30 min. Then, 0.3 g (911 µmol) of sulfide A and 0.9 mL of ethyl acetate were added. After 16.5 hours, a small amount of the reaction mixture was analyzed under HPLC analysis condition 1.

<Content> sulfoxide A 88%; sulfone A 8%; sulfide A 4%
<Enantiomer excess of sulfoxide A> 96% ee

Example 16

Addition of Diphenyl Sulfide

Reaction was performed in the same manner as in Example 15 except for using diphenyl sulfide instead of dibutyl sulfide as an additive. After 16.5 hours, a small amount of the reaction mixture was analyzed under HPLC analysis condition 1.

<Content> sulfoxide A 88%; sulfone A 11%; sulfide A 1%
<Enantiomer excess of sulfoxide A> 99.5% ee To the mixture were added 3.7 mL of 8% aqueous sodium hydrogen carbonate solution, 1.4 g of sodium thiosulfate 5H$_2$O and 1.4 mL of water, and the mixture was heated to 25° C. and stirred. After removing the aqueous layer, the organic layer was washed twice with 1 mL of 8% aqueous sodium hydrogen carbonate solution, and the product was extracted from the organic layer twice with 1 mL of 1M aqueous sodium hydroxide solution and 1 mL of 0.75M aqueous sodium hydroxide solution. The combined aqueous layers were neutralized with acetic acid and extracted twice with 2 mL of 4-methyl-2-pentanone. The combined organic layers were analyzed under HPLC analysis condition 1.

<Content> sulfoxides A 89%; sulfone A 11%; sulfide A 0%
<Enantiomer excess of sulfoxide A> 99.7% ee

Example 17

Production of S-Lansoprazole 234 mg (808 µmol) of S-dichloro chiral ligand, 94.9 mg (269 µmol) of iron(III) acetylacetonate and 23.2 mg (136 µmol) of lithium 4-dimethylaminobenzoate were suspended in 7.5 mL of ethyl acetate at 25° C., and stirred for more than 30 min. To the mixture were added 1.00 g (2.69 mmol) of the sulfide monohydrate of lansoprazole and 7.5 mL of ethyl acetate. After the mixture was cooled to −5° C. at a rate of 1° C. per min, 550 µL (5.39 µmol) of 30% aqueous hydrogen peroxide solution was added dropwise for more than 2 min. After 20.5 hours, the reaction mixture was analyzed under HPLC analysis condition 2 and HPLC analysis condition 3.

<Content> sulfoxide 87%; sulfone 12%; sulfide 1%
<Enantiomer excess of sulfoxide> 98% ee To the mixed solution was added 5 mL of the mixed solvent of a saturated aqueous sodium thiosulfate solution and a saturated aqueous sodium hydrogen carbonate. The mixture was heated to 5° C. and stirred. After removing the aqueous layer, the organic layer was concentrated under a reduced pressure.

<Content> sulfoxide form 86%; sulfone 13%; sulfide 1%
<Enantiomer excess of sulfoxide> 98% ee After treatment by silica gel column chromatography (eluent: mixed solvent of ethyl acetate and methanol) was conducted to give 0.86 g of the title compound (purity 98%; 97% ee).

$^1$H-NMR (400 MHz, DMSO): δ 13.6 (1H, s), 8.29 (1H, d), 7.65 (1H, br s), 7.31 (2H, m), 7.10 (1H, d), 4.92 (2H, q), 4.80 (2H, q, —SOCH$_2$—), 2.18 (3H, s)

LRMS: [M+Na]$^+$ Calcd. 392.07. Found 392.40.

The configuration of sulfoxide in the obtained optically active lansoprazole was estimated to be S configuration, based on the behavior and the retention time in HPLC of omeprazole and pantoprazole.

Example 18

Production of S-Rabeprazole 253 mg (874 µmol) of S-dichloro chiral ligand, 103 mg (291 µmol) of iron(III) acetylacetonate and 25.2 mg (147 µmol) of lithium 4-dimethylaminobenzoate were suspended in 5 mL ethyl acetate at 25° C., and stirred for more than 30 min. To the mixture were added 1.00 g (2.91 mmol) of the sulfide of rabeprazole and 5 mL ethyl acetate. After the mixture was cooled to −5° C. at a rate of 1° C. per min, 595 µL (5.82 mmol) of 30% aqueous hydrogen peroxide solution was added dropwise for more than 2 min. After 21.5 hours, the reaction mixture was analyzed under HPLC analysis condition 2 and HPLC analysis condition 3.

<Content> sulfoxide 82%; sulfone 17%; sulfide 1%
<Enantiomer excess of sulfoxide> 97% ee To the mixed solution was added 5 mL of the mixed solvent of a saturated aqueous sodium thiosulfate solution and a saturated aqueous sodium hydrogen carbonate. The mixture was heated to 5° C. and stirred. After removing the aqueous layer, the organic layer was concentrated under a reduced pressure.

<Content> sulfoxide 82%; sulfone 18%; sulfide 0%
<Enantiomer excess of sulfoxide> 97% ee After treatment by silica gel column chromatography (eluent: mixed solvent of ethyl acetate and methanol) was conducted to give 0.73 g of the title compound (purity 97%; 96% ee).

$^1$H-NMR (400 MHz, DMSO): δ 13.5 (1H, s), 8.21 (1H, d), 7.65 (1H, br s), 7.31 (2H, m), 6.96 (1H, d), 4.75 (2H, q, —SOCH$_2$—), 4.10 (2H, d), 3.48 (2H, t), 3.25 (3H, s), 2.14 (3H, s), 1.99 (2H, m)

LRMS: [M+Na]$^+$ Calcd. 382.12. Found 382.44.

The configuration of sulfoxide in the obtained optically active rabeprazole was estimated to be S configuration, based on the behavior and the retention time in HPLC of omeprazole and pantoprazole.

Example 19

Production of S-Pantoprazole 237 mg (815 µmol) of S-dichloro chiral ligand, 95.8 mg (271 µmol) of iron(III) acetylacetonate and 23.4 mg (137 µmol) of lithium 4-dimethylaminobenzoate were suspended in 5 mL of ethyl acetate at 25° C., and stirred for more than 30 min. To the mixture were added 1.00 g (2.72 mmol) of the sulfide of pantoprazole and 5 mL of ethyl acetate. After the mixture was cooled to −8° C. at a rate of 1° C. per min, 556 µL (5.44 mmol) of 30% aqueous hydrogen peroxide solution was added dropwise for more than 1 min. After 44 hours, the reaction mixture was analyzed under HPLC analysis condition 2 and HPLC analysis condition 3.

<Content> sulfoxide 75%; sulfone 13%; sulfide 12%
<Enantiomer excess of sulfoxide> 83% ee To the mixed solution was added 5 mL of the mixed solvent of a saturated aqueous sodium thiosulfate solution and a saturated aqueous sodium hydrogen carbonate. The mixture was heated to 10° C. and stirred. After removing the aqueous layer, the organic layer was concentrated under a reduced pressure.

<Content> sulfoxide 75%; sulfide 13%; sulfide 12%
<Enantiomer excess of sulfoxide> 83% ee After treatment by silica gel column chromatography (eluent: mixed solvent of ethyl acetate and methanol) was conducted to give 0.74 g of the title compound (purity: 95.13%; 82% ee).

$^1$H-NMR (400 MHz, DMSO): δ 13.8 (1H, s), 8.15 (1H, d), 7.72 (1H, d), 7.44 (1H, s), 7.26 (1H, t), 7.16 (1H, dd), 7.11 (1H, d), 4.69 (2H, q, —SOCH$_2$—), 3.90 (3H, s), 3.77 (3H, s)

LRMS: [M+Na]$^+$ Calcd. 406.06. Found 406.36.

Optical rotation $[\alpha]_D^{25}$: −79.4 (c 0.3, MeOH)

Tetrahedron: Asymmetry, 2012, 23, 457-460 describes that optical rotation $[\alpha]_D^{25}$ of S-form of pantoprazole (96% ee) is −95.5 (c 0.3, MeOH).

The analysis results of the reactions of Examples 17 to 19 and Example 1 are summarized in Table 4.

TABLE 4

| | Reaction time | Content (%) | | | % ee |
| --- | --- | --- | --- | --- | --- |
| | | Sulfoxide | Sulfone | Sulfide | |
| Example 17 | S-lansoprazole | 20.5 hr | 87 | 12 | 1 | 98 |
| Example 18 | S-rabeprazole | 21.5 hr | 82 | 17 | 1 | 97 |
| Example 19 | S-pantoprazole | 44 hr | 75 | 13 | 12 | 83 |
| Example 1 | S-sulfoxide A (esomeprazole) | 4.5 hr | 88 | 11 | 0 | 98 |

As described above, it is understood that various optically active proton pump inhibitor compounds can be produced in a high yield and enantioselectivity by a production method of the present invention.

Example 20

Scale Change of Production of S-Sulfoxide A (Esomeprazole)

As described in Non-Patent Literature 1 and the like, when using titanium as a catalyst, there was a problem that it was necessary to increase the catalyst amount upon scaling up the reaction. Accordingly, experiments using 1 g, 20 g and 100 g of the starting sulfide A were conducted in a production method of the present invention. The reaction using 100 g is described below, but the reactions were similarly conducted using the corresponding amount of reagents in case of using 1 g or 20 g.

7.93 g (27.3 mmol) of S-dichloro chiral ligand, 8.04 g (22.77 mmol) of iron(III) acetylacetonate and 3.9 g (22.77 mmol) of lithium 4-dimethylaminobenzoate were suspended in 300 mL of ethyl acetate at room temperature, and stirred for more than 30 min. To the mixture were added 100 g (303.56 mmol) of sulfide A and 500 mL of ethyl acetate. After the mixture was cooled to −5° C., 68.82 g (607.12 mmol) of 30% aqueous hydrogen peroxide solution was added dropwise. After 8 hours, the reaction mixture was analyzed under HPLC analysis condition 3.

The analysis results of the reactions in these various scales are shown in Table 5 below.

TABLE 5

| Amount of Sulfide A | Content (%) | | | % ee |
| --- | --- | --- | --- | --- |
| | Sulfoxide A | Sulfone A | Sulfide A | |
| 1 g | 88.3 | 10.2 | 1.5 | 96.3 |
| 20 g | 85.8 | 13.7 | 0.5 | 97.0 |
| 20 g | 85.4 | 13.7 | 0.8 | 95.6 |
| 100 g | 86.5 | 11.8 | 1.7 | 95.1 |

As described above, good reproducibility is observed in a production method of the present invention. It is understood that high yield and enantioselectivity can be maintained even in an increased scale, and it is not necessary to increase the amount of the catalyst.

INDUSTRIAL APPLICABILITY

A highly pure optically active proton pump inhibitor compound can be produced safely and inexpensively in a high yield and enantioselectivity by a production method of the present invention.

The invention claimed is:

1. An iron complex coordinated with a chiral ligand of Formula 4:

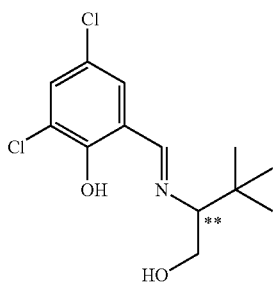

(4)

wherein ** represents R configuration or S configuration.

2. A combination comprising the iron complex of claim 1 and an optionally substituted benzoic acid or a salt thereof.